US009049859B2

(12) United States Patent
Gewehr et al.

(10) Patent No.: US 9,049,859 B2
(45) Date of Patent: Jun. 9, 2015

(54) PESTICIDAL MIXTURES

(71) Applicants: Markus Gewehr, Kastellaun (DE); Robert John Gladwin, Macclesfield (GB); Lutz Brahm, Worms (DE)

(72) Inventors: Markus Gewehr, Kastellaun (DE); Robert John Gladwin, Macclesfield (GB); Lutz Brahm, Worms (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/265,870

(22) Filed: Apr. 30, 2014

(65) Prior Publication Data
US 2014/0323311 A1 Oct. 30, 2014

Related U.S. Application Data

(63) Continuation of application No. 13/513,675, filed as application No. PCT/EP2010/068786 on Dec. 3, 2010, now Pat. No. 8,748,342.

(30) Foreign Application Priority Data

Dec. 8, 2009 (EP) .................................. 09178364

(51) Int. Cl.
| A01N 25/26 | (2006.01) |
| A01N 43/40 | (2006.01) |
| A01N 43/36 | (2006.01) |
| A01N 43/00 | (2006.01) |
| A01N 37/40 | (2006.01) |
| A01N 37/10 | (2006.01) |
| A01N 37/44 | (2006.01) |
| A01N 39/02 | (2006.01) |
| A01N 39/04 | (2006.01) |
| A01N 43/42 | (2006.01) |
| A01N 43/56 | (2006.01) |
| A01N 43/78 | (2006.01) |

(52) U.S. Cl.
CPC ............... *A01N 37/40* (2013.01); *A01N 37/10* (2013.01); *A01N 37/44* (2013.01); *A01N 39/02* (2013.01); *A01N 39/04* (2013.01); *A01N 43/40* (2013.01); *A01N 43/42* (2013.01); *A01N 43/56* (2013.01); *A01N 43/78* (2013.01)

(58) Field of Classification Search
USPC .................... 504/100, 130, 138, 139
See application file for complete search history.

(56) References Cited

U.S. PATENT DOCUMENTS

| 5,330,995 A | 7/1994 | Eicken et al. |
| 5,438,070 A | 8/1995 | Eicken et al. |
| 6,147,104 A | 11/2000 | Eicken et al. |
| 8,008,232 B2 | 8/2011 | Gewehr et al. |
| 2004/0204470 A1 | 10/2004 | Elbe et al. |
| 2004/0209923 A1 | 10/2004 | Berger et al. |
| 2006/0079561 A1 | 4/2006 | Lahm et al. |
| 2006/0089399 A1 | 4/2006 | Dunkel et al. |
| 2006/0211771 A1 | 9/2006 | Elbe et al. |
| 2007/0082877 A1 | 4/2007 | Dunkel et al. |
| 2007/0265267 A1 | 11/2007 | Walter et al. |
| 2008/0015244 A1 | 1/2008 | Dunkel et al. |
| 2008/0108686 A1 | 5/2008 | Gewehr et al. |
| 2008/0139389 A1 | 6/2008 | Kneen et al. |
| 2008/0153707 A1 | 6/2008 | Gewehr et al. |
| 2008/0255071 A1 | 10/2008 | Suty-Heinze et al. |
| 2008/0269051 A1 | 10/2008 | Suty-Heinze et al. |
| 2008/0293566 A1 | 11/2008 | Suty-Heinze et al. |
| 2008/0293798 A1 | 11/2008 | Dietz et al. |
| 2009/0036509 A1 | 2/2009 | Gewehr et al. |
| 2009/0105077 A1 | 4/2009 | Bhatti et al. |
| 2009/0118346 A1 | 5/2009 | Dunkeel et al. |
| 2009/0233916 A1 | 9/2009 | Kohle et al. |
| 2009/0247511 A1 | 10/2009 | Suty-Heinze et al. |
| 2009/0286681 A1 | 11/2009 | Dahmen et al. |
| 2009/0318291 A1 | 12/2009 | Dietz et al. |
| 2011/0046123 A1 | 2/2011 | Jamet et al. |
| 2011/0203018 A1 | 8/2011 | Gewehr et al. |
| 2011/0218100 A1 | 9/2011 | Dahmen et al. |
| 2011/0263423 A1 | 10/2011 | Wilhelm et al. |
| 2012/0021905 A1 | 1/2012 | Voeste et al. |
| 2013/0053241 A1 | 2/2013 | Dahmen et al. |

FOREIGN PATENT DOCUMENTS

| CA | 2 304 093 | 4/1999 |
| CA | 2 491 368 | 1/2004 |
| CA | 2 081 935 | 5/2004 |
| CA | 2 105 503 | 11/2004 |

(Continued)

OTHER PUBLICATIONS

Office Action dated Mar. 5, 2014, from U.S. Appl. No. 12/865,883.
Office Action dated Apr. 9, 2014 from U.S. Appl. No. 13/124,940.
Lancaster, Sarah H., et al. "Sicklepod (*Senna obtusifolia*) control and seed prodiction after 2,4-DB applied alone and with fungicides or insecticides", Weed Technology, 2995, pp. 451-455, vol. 19.

(Continued)

*Primary Examiner* — Alton Pryor
(74) *Attorney, Agent, or Firm* — Brinks Gilson & Lione

(57) ABSTRACT

The present invention relates to an agrochemical mixture for increasing the health of a plant, comprising as active ingredients a herbicidal compound (I) selected from the group consisting of: Benzoic acids, Pyridine carboxylic acids, Quinoline carboxylic acids, and benazolin-ethyl; and a fungicidal compound (II) in synergistically effective amounts. The present invention further relates to a method for improving the health of a plant, wherein the plant, the locus where the plant is growing or is expected to grow or plant propagation material from which the plant grows is treated with an effective amount of a mixture as defined above. In addition, the invention relates to the use of a mixture as defined above for synergistically increasing the health of a plant.

9 Claims, No Drawings

(56) References Cited

FOREIGN PATENT DOCUMENTS

| | | |
|---|---|---|
| CA | 2 597 022 | 8/2006 |
| CA | 2 616 719 | 3/2007 |
| CA | 2 476 462 | 4/2011 |
| CA | 2 514 379 | 4/2012 |
| EP | 0 133 028 | 2/1985 |
| EP | 0 737 682 | 10/1996 |
| EP | 0 545 099 | 3/1997 |
| EP | 0 824 099 | 2/1998 |
| EP | 0 589 301 | 6/2002 |
| EP | 1 829 865 | 9/2004 |
| EP | 1 922 927 | 5/2008 |
| EP | 2 039 772 | 3/2009 |
| EP | 2 100 505 | 9/2009 |
| WO | WO 99/09013 | 2/1999 |
| WO | WO 03/010149 | 2/2003 |
| WO | WO 03/070705 | 8/2003 |
| WO | WO 03/070708 | 8/2003 |
| WO | WO 03/074491 | 9/2003 |
| WO | WO 2004/005242 | 1/2004 |
| WO | WO 2004/035589 | 4/2004 |
| WO | WO 2004/067515 | 8/2004 |
| WO | WO 2005/018324 | 3/2005 |
| WO | WO 2005/122770 | 12/2005 |
| WO | WO 2005/123689 | 12/2005 |
| WO | WO 2005/123690 | 12/2005 |
| WO | WO 2006/015865 | 2/2006 |
| WO | WO 2006/015866 | 2/2006 |
| WO | WO 2006/035316 | 4/2006 |
| WO | WO 2006/036827 | 4/2006 |
| WO | WO 2006/037632 | 4/2006 |
| WO | WO 2006/040123 | 4/2006 |
| WO | WO 2006/087343 | 8/2006 |
| WO | WO 2006/092213 | 9/2006 |
| WO | WO 2006/105888 | 10/2006 |
| WO | WO 2006/105889 | 10/2006 |
| WO | WO 2006/114212 | 11/2006 |
| WO | WO 2007/017256 | 2/2007 |
| WO | WO 2007/017409 | 2/2007 |
| WO | WO 2007/017416 | 2/2007 |
| WO | WO 2007/031141 | 3/2007 |
| WO | WO 2007/071656 | 6/2007 |
| WO | WO 2007/104669 | 9/2007 |
| WO | WO 2007/115765 | 10/2007 |
| WO | WO 2007/115766 | 10/2007 |
| WO | WO 2007/124907 | 11/2007 |
| WO | WO 2007/128756 | 11/2007 |
| WO | WO 2007/134776 | 11/2007 |
| WO | WO 2008/000377 | 1/2008 |
| WO | WO 2008/087182 | 7/2008 |
| WO | WO 2008/095890 | 8/2008 |
| WO | WO 2008/098928 | 8/2008 |
| WO | WO 2009/098218 | 8/2009 |
| WO | WO 2009/098223 | 8/2009 |
| WO | WO 2009/098225 | 8/2009 |
| WO | WO 2010/046380 | 4/2010 |
| WO | WO 2010/079176 | 7/2010 |
| WO | WO 2010/149732 | 12/2010 |
| WO | WO 2011/069893 | 6/2011 |

OTHER PUBLICATIONS

Tomlin, C.D.S., "The Pesticide Manual", (2003), pp. 1337-1344, BCPC, Alton, Hampshire.

Behrens, Mark R., et al., "Dicamba Resistance: Enlarging and preserving biotechnology based weed management strategies", Science, 2007, p. 1185-1188, vol. 316.

Office Action dated Jul. 11, 2012, from U.S. Appl. No. 12/865,883.

Office Action dated Jan. 8, 2013, from U.S. Appl. No. 12/865,883.

Office Action dated Sep. 17, 2013 from U.S. Appl. No. 13/124,940.

PESTICIDAL MIXTURES

This application is a continuation of U.S. application No. 13/513,675, filed Jun. 4, 2012, the entire contents of which are hereby incorporated by reference. U.S. application Ser. No. 13/513,675, is a National Stage application of International Application No. PCT/EP2010/068786, filed Dec. 3, 2010, and claims priority under 35 U.S.C. § 119 to European Patent Application No. 09178364.7, filed Dec. 8, 2009, the entire contents of which are hereby incorporated herein by reference.

The present invention relates to an agrochemical mixture for increasing the health of a plant, comprising as active ingredients
1) a herbicidal compound (I) selected from the group consisting of:
   (i) Benzoic acids, selected from chloramben, dicamba and 2,3,6-TBA;
   (ii) Pyridine carboxylic acids, selected from clopyralid, fluroxypyr, picloram and triclopyr;
   (iii) Quinoline carboxylic acids, selected from quinclorac and quinmerac;
   (iv) benazolin-ethyl; and
2) a fungicidal compound (II) selected from the group consisting of N-(3',4',5'-trifluorobiphenyl-2-yl)-3-difluoromethyl-1-methyl-1H-pyrazole-4-carboxamide (common name: fluxapyroxad), N-[2-(4'-trifluoromethylthio)-biphenyl]-3-difluoromethyl-1-methyl-1H-pyrazole-4-carboxamide, N-(3',4'-dichloro-5-fluorobiphenyl-2-yl)-3-difluoromethyl-1-methylpyrazole-4-carboxamide (common name: bixafen), N-[2-(1,3-dimethylbutyl)-phenyl]-1,3-dimethyl-5-fluoro-1H-pyrazole-4-carboxamide (common name: penflufen), N-(2-bicyclopropyl-2-yl-phenyl)-3-difluoromethyl-1-methyl-1H-pyrazole-4-carboxamide (common name: sedaxane), N-[1,2,3,4-tetrahydro-9-(1-methylethyl)-1,4-methanonaphthalen-5-yl]-3-(difluoromethyl)-1-methyl-1H-pyrazole-4-carboxamide (common name: isopyrazam), N-[2-(1,3-dimethylbutyl)-3-thienyl]-1-methyl-3-(trifluoromethyl)-1H-pyrazole-4-carboxamide (common name: penthiopyrad), boscalid, fluopyram, flutolanil, furametpyr, mepronil and thifluzamide
in synergistically effective amounts.

The present invention further relates to a pesticidal composition, comprising a liquid or solid carrier and a mixture as defined above.

In addition, the present invention relates to a method for improving the health of a plant, wherein the plant, the locus where the plant is growing or is expected to grow or plant propagation material from which the plant grows is treated with an effective amount of a mixture as defined above. In particular, the present invention relates to a method for increasing the yield of a plant, wherein the plant, the locus where the plant is growing or is expected to grow or plant propagation material from which the plant grows is treated with an effective amount of a mixture as defined above.

The present invention additionally relates to the use of a mixture comprising a herbicide as compound (I) and a fungicidal compound (II) as defined above for synergistically increasing the health of a plant.

The compounds (I) and (II) as well as their pesticidal action and methods for producing them are generally known. For instance, the commercially available compounds may be found in The Pesticide Manual, 14th Edition, British Crop Protection Council (2006) among other publications.

Suitable salts of dicamba include those salts of dicamba, where the counterion is an agriculturally acceptable cation. Suitable examples of such salts are dicamba-sodium, dicamba-potassium, dicamba-methylammonium, dicamba-dimethylammonium, dicamba-isopropylammonium, dicamba-diglycolamine, dicamba-olamine, dicamba-diolamine and dicamba-trolamine. Examples of a suitable ester are dicamba-methyl and dicamba-butoyl. Suitable salts of clopyralid are clopyralid potassium, clopyralid olamine and clopyralid triisopropanolammonium. Examples of a suitable ester of fluroxypyr are fluroxypyr-meptyl and fluroxypyr-2-butoxy-1-methylethyl. Suitable salts of picloram are picloram dimethylammonium, picloram potassium, picloram triisopropanolammonium, picloram triisopropylammonium and picloram trolamine. A suitable ester of picloram is picloram-isoctyl. A suitable salt of triclopyr is triclopyr triethalammonium. A suitable ester of triclopyr is triclopyr-butotyl.

The amides (compound II) are known as fungicides (cf., for example, EP-A 545 099, EP-A 589 301, EP-A 737682, EP-A 824099, WO 99/09013, WO 03/010149, WO 03/070705, WO 03/074491, WO 04/005242, WO 04/035589, WO 04/067515, WO 06/087343,). They can be prepared in the manner described therein.

Lancaster et al. (Sicklepod (*Senna obtusifolia*) control and seed production after 2,4-DB applied alone and with fungicides or insecticides. Weed Technology 2005. Volume 19: 451-455) disclose the use of pesticidal mixtures containing a fungicide (such as boscalid) or an insecticide (such as acephate) with 2,4-DB for controlling the weed sicklepod.

WO 05/018324 discloses a method for treating plants in need of growth promotion, comprising applying to said plants, to the seeds from which they grow or to the locus in which they grow, a non-phytotoxic, effective plant growth promoting amount of an amide compound.

WO 08/095890 is directed to fungicidal mixtures, comprising at least one carboxanilide and at least one further fungicide and to methods for controlling harmful fungi using these mixtures.

WO 09/098218 relates to a method for improving the plant health of at least one plant variety, which method comprises treating the plant and/or the locus where the plant is growing or is intended to grow with a mixture comprising an amide and a further fungicide or an insecticide or a herbicide wherein the herbicide is selected from the group consisting of glyphosate, glyphosinate and sulfonisate.

WO 09/118161 describes a method of plant treatment that is able to induce positive growth regulating responses by applying certain amid compounds, in particular nicotinamide compounds.

Methods of improving plant health by the application of dicamba are disclosed in US 2009/0105077.

None of these references, however, disclose the synergistic increase of the health of a plant based on the application of the mixtures as defined at the outset.

In crop protection, there is a continuous need for compositions that improve the health of plants. Healthier plants are desirable since they result in better crop yields and/or a better quality of the plants or crops. Healthier plants also better resist to biotic and/or abiotic stress. A high resistance against biotic stresses in turn allows the person skilled in the art to reduce the quantity of pesticides applied and consequently to slow down the development of resistances against the respective pesticides.

It was therefore an object of the present invention to provide a pesticidal composition comprising an agrochemical mixture which solves the problems outlined above, and which should, in particular improve the health of plants, in particular the yield of plants.

We have found that these objects are in part or in whole achieved by the mixtures comprising the active ingredients as defined in the outset. We have found that simultaneous, that is joint or separate application of the compound (I) and the compound (II) or successive application of compound (I) and the compound (II) provides enhanced plant health effects compared to the plant health effects that are possible with the individual compounds, in particular enhanced yield effects compared to the yield effects that are possible with the individual compounds (synergistic effect).

Binary mixtures that can be used in the methods of the present invention are listed in table 1 below, wherein compound (I) is selected from the group consisting of:
(i) Benzoic acids, selected from chloramben (I-1), dicamba (I-2) and 2,3,6-TBA (I-3);
(ii) Pyridine carboxylic acids, selected from clopyralid (I-4), fluroxypyr (I-5), picloram (I-6) and triclopyr (I-7);
(iii) Quinoline carboxylic acids, selected from quinclorac (I-8) and quinmerac (I-9);
(iv) benazolin-ethyl (I-10); and
wherein compound (II) is selected from the group consisting of N-(3',4',5'-trifluorobiphenyl-2-yl)-3-difluoromethyl-1-methyl-1H-pyrazole-4-carboxamide (common name: fluxapyroxad) (11-1), N-[2-(4'-trifluoromethylthio)-biphenyl]-3-difluoromethyl-1-methyl-1H-pyrazole-4-carboxamide (II-2), N-(3',4'-dichloro-5-fluorobiphenyl-2-yl)-3-difluoromethyl-1-methylpyrazole-4-carboxamide (common name: bixafen) (II-3), N-[2-(1,3-dimethylbutyl)-phenyl]-1,3-dimethyl-5-fluoro-1H-pyrazole-4-carboxamide (common name: penflufen) (II-4), N-(2-bicyclopropyl-2-yl-phenyl)-3-difluoromethyl-1-methyl-1H-pyrazole-4-carboxamide (common name: sedaxane) (II-5), N-[1,2,3,4-tetrahydro-9-(1-methylethyl)-1,4-methanonaphthalen-5-yl]-3-(difluoromethyl)-1-methyl-1H-pyrazole-4-carboxamide (common name: isopyrazam) (II-6), N-[2-(1,3-dimethylbutyl)-3-thienyl]-1-methyl-3-(trifluoromethyl)-1H-pyrazole-4-carboxamide (common name: penthiopyrad) (II-7), boscalid (II-8), fluopyram (II-9), flutolanil (II-10), furametpyr (II-11), mepronil (II-12) and thifluzamide (II-13).

In a preferred embodiment of the invention, the mixture comprises a herbicidal compound (I) selected from the group consisting of dicamba, clopyralid, fluroxypyr, picloram, triclopyr, quinclorac and quinmerac. In an even more preferred embodiment of the invention, the mixture comprises a herbicidal compound (I) selected from the group consisting of dicamba, quinclorac and quinmerac. Most preferred compound (I) is dicamba.

In a preferred embodiment of the invention, the mixture comprises a fungicidal compound (II) selected from the group consisting of fluxapyroxad, bixafen, boscalid, fluopyram, isopyrazam, penflufen, penthiopyrad and sedaxane. In an even more preferred embodiment of the invention, the mixture comprises a fungicidal compound (II) selected from the group consisting of fluxapyroxad, bixafen, boscalid, fluopyram, isopyrazam and penthiopyrad. In a most preferred embodiment, compound (II) is fluxapyroxad. In another most preferred embodiment, compound (II) is boscalid.

With respect to their intended use in the methods of the present invention, the following binary mixtures listed in table 1 comprising one compound (I) and one compound (II) are a preferred embodiment of the present invention.

TABLE 1

| Mixture | Compound (I) | (II) |
|---|---|---|
| M-1 | I-1 | II-1 |
| M-2 | I-2 | II-1 |
| M-3 | I-3 | II-1 |
| M-4 | I-4 | II-1 |
| M-5 | I-5 | II-1 |
| M-6 | I-6 | II-1 |
| M-7 | I-7 | II-1 |
| M-8 | I-8 | II-1 |
| M-9 | I-9 | II-1 |
| M-10 | I-10 | II-1 |
| M-11 | I-1 | II-2 |
| M-12 | I-2 | II-2 |
| M-13 | I-3 | II-2 |
| M-14 | I-4 | II-2 |
| M-15 | I-5 | II-2 |
| M-16 | I-6 | II-2 |
| M-17 | I-7 | II-2 |
| M-18 | I-8 | II-2 |
| M-19 | I-9 | II-2 |
| M-20 | I-10 | II-2 |
| M-21 | I-1 | II-3 |
| M-22 | I-2 | II-3 |
| M-23 | I-3 | II-3 |
| M-24 | I-4 | II-3 |
| M-25 | I-5 | II-3 |
| M-26 | I-6 | II-3 |
| M-27 | I-7 | II-3 |
| M-28 | I-8 | II-3 |
| M-29 | I-9 | II-3 |
| M-30 | I-10 | II-3 |
| M-31 | I-1 | II-4 |
| M-32 | I-2 | II-4 |
| M-33 | I-3 | II-4 |
| M-34 | I-4 | II-4 |
| M-35 | I-5 | II-4 |
| M-36 | I-6 | II-4 |
| M-37 | I-7 | II-4 |
| M-38 | I-8 | II-4 |
| M-39 | I-9 | II-4 |
| M-40 | I-10 | II-4 |
| M-41 | I-1 | II-5 |
| M-42 | I-2 | II-5 |
| M-43 | I-3 | II-5 |
| M-44 | I-4 | II-5 |
| M-45 | I-5 | II-5 |
| M-46 | I-6 | II-5 |
| M-47 | I-7 | II-5 |
| M-48 | I-8 | II-5 |
| M-49 | I-9 | II-5 |
| M-50 | I-10 | II-5 |
| M-51 | I-1 | II-6 |
| M-52 | I-2 | II-6 |
| M-53 | I-3 | II-6 |
| M-54 | I-4 | II-6 |
| M-55 | I-5 | II-6 |
| M-56 | I-6 | II-6 |
| M-57 | I-7 | II-6 |
| M-58 | I-8 | II-6 |
| M-59 | I-9 | II-6 |
| M-60 | I-10 | II-6 |
| M-61 | I-1 | II-7 |
| M-62 | I-2 | II-7 |
| M-63 | I-3 | II-7 |
| M-64 | I-4 | II-7 |
| M-65 | I-5 | II-7 |
| M-66 | I-6 | II-7 |
| M-67 | I-7 | II-7 |
| M-68 | I-8 | II-7 |
| M-69 | I-9 | II-7 |
| M-70 | I-10 | II-7 |
| M-71 | I-1 | II-8 |
| M-72 | I-2 | II-8 |
| M-73 | I-3 | II-8 |
| M-74 | I-4 | II-8 |
| M-75 | I-5 | II-8 |
| M-76 | I-6 | II-8 |
| M-77 | I-7 | II-8 |
| M-78 | I-8 | II-8 |

TABLE 1-continued

| Mixture | Compound (I) | (II) |
|---|---|---|
| M-79 | I-9 | II-8 |
| M-80 | I-10 | II-8 |
| M-81 | I-1 | II-9 |
| M-82 | I-2 | II-9 |
| M-83 | I-3 | II-9 |
| M-84 | I-4 | II-9 |
| M-85 | I-5 | II-9 |
| M-86 | I-6 | II-9 |
| M-87 | I-7 | II-9 |
| M-88 | I-8 | II-9 |
| M-89 | I-9 | II-9 |
| M-90 | I-10 | II-9 |
| M-91 | I-1 | II-10 |
| M-92 | I-2 | II-10 |
| M-93 | I-3 | II-10 |
| M-94 | I-4 | II-10 |
| M-95 | I-5 | II-10 |
| M-96 | I-6 | II-10 |
| M-97 | I-7 | II-10 |
| M-98 | I-8 | II-10 |
| M-99 | I-9 | II-10 |
| M-100 | I-10 | II-10 |
| M-101 | I-1 | II-11 |
| M-102 | I-2 | II-11 |
| M-103 | I-3 | II-11 |
| M-104 | I-4 | II-11 |
| M-105 | I-5 | II-11 |
| M-106 | I-6 | II-11 |
| M-107 | I-7 | II-11 |
| M-108 | I-8 | II-11 |
| M-109 | I-9 | II-11 |
| M-110 | I-10 | II-11 |
| M-111 | I-1 | II-12 |
| M-112 | I-2 | II-12 |
| M-113 | I-3 | II-12 |
| M-114 | I-4 | II-12 |
| M-115 | I-5 | II-12 |
| M-116 | I-6 | II-12 |
| M-117 | I-7 | II-12 |
| M-118 | I-8 | II-12 |
| M-119 | I-9 | II-12 |
| M-120 | I-10 | II-12 |
| M-121 | I-1 | II-13 |
| M-122 | I-2 | II-13 |
| M-123 | I-3 | II-13 |
| M-124 | I-4 | II-13 |
| M-125 | I-5 | II-13 |
| M-126 | I-6 | II-13 |
| M-127 | I-7 | II-13 |
| M-128 | I-8 | II-13 |
| M-129 | I-9 | II-13 |
| M-130 | I-10 | II-13 |

Within the binary mixtures of table 1, the following mixtures are preferred: M-2, M-4, M-5, M-6, M-7, M-8, M-9, M-22, M-24, M-25, M-26, M-27, M-28, M-29, M-32, M-34, M-35, M-36, M-37, M-38, M-39, M-42, M-44, M-45, M-46, M-47, M-48, M-49, M-52, M-54, M-55, M-56, M-57, M-58, M-59, M-62, M-64, M-65, M-66, M-67, M-68, M-69, M-72, M-74, M-75, M-76, M-77, M-78, M-79, M-82, M-84, M-85, M-86, M-87, M-88 and M-89.

Within this subset, the following mixtures are especially preferred: M-2, M-4, M-5, M-6, M-7, M-8, M-9, M-22, M-28, M-29, M-32, M-38, M-39, M-42, M-48, M-49, M-52, M-58, M-59, M-62, M-68, M-69, M-72, M-74, M-75, M-76, M-77, M-78, M-79, M-82, M-88 and M-89.

The following mixtures are even more preferred: M-2, M-8, M-9, M-72, M-78 and M-79. Most preferred mixtures are M-2 and M-72.

Preferred for the use within the methods according to the invention are, in particular, the following mixtures: M-2, M-4, M-5, M-6, M-7, M-8, M-9, M-22, M-24, M-25, M-26, M-27, M-28, M-29, M-32, M-34, M-35, M-36, M-37, M-38, M-39, M-42, M-44, M-45, M-46, M-47, M-48, M-49, M-52, M-54, M-55, M-56, M-57, M-58, M-59, M-62, M-64, M-65, M-66, M-67, M-68, M-69, M-72, M-74, M-75, M-76, M-77, M-78, M-79, M-82, M-84, M-85, M-86, M-87, M-88 and M-89. Especially preferred for the use within the methods according to the invention are, in particular, the following mixtures: M-2, M-4, M-5, M-6, M-7, M-8, M-9, M-22, M-28, M-29, M-32, M-38, M-39, M-42, M-48, M-49, M-52, M-58, M-59, M-62, M-68, M-69, M-72, M-74, M-75, M-76, M-77, M-78, M-79, M-82, M-88 and M-89. Even more preferred for the use within the methods according to the invention are, in particular, the following mixtures: M-2, M-8, M-9, M-72, M-78. Most preferred for the use within the methods according to the invention are M-2 and M-72.

The inventive mixtures can further contain at least one additional compound (III) selected from the group consisting of insecticides, fungicides, herbicides and plant growth regulators.

All mixtures set forth above are also an embodiment of the present invention.

The remarks as to preferred mixtures comprising compounds selected from the groups consisting of compounds (I) and (II), to their preferred use and methods of using them are to be understood either each on their own or preferably in combination with each other.

In the terms of the present invention "mixture" is not restricted to a physical mixture comprising one compound (I) and one compound (II) but refers to any preparation form of one compound (I) and one compound (II), the use of which is time- and locus-related.

In one embodiment of the invention "mixture" refers to a binary mixture comprising one compound (I) and one compound (II).

In another embodiment of the invention, "mixture" refers to one compound (I) and one compound (II) formulated separately but applied to the same plant, plant propagule or locus in a temporal relationship, i.e. simultaneously or subsequently, the subsequent application having a time interval which allows a combined action of the compounds.

In another embodiment of the invention, one compound (I) and one compound (II) are applied simultaneously, either as a mixture or separately, or subsequently to plant propagules.

In a preferred embodiment of the invention, one compound (I) and one compound (II) are applied simultaneously, either as a mixture or separately, as foliar spray treatment.

Furthermore, the individual compounds of the mixtures according to the invention such as parts of a kit or parts of the binary mixture may be mixed by the user himself in a spray tank and further auxiliaries may be added if appropriate (tank mix).

The plants to be treated according to the invention are selected from the group consisting of agricultural, silvicultural, ornamental and horticultural plants, each in its natural or genetically modified form, more preferably from agricultural plants.

In one embodiment, the method for increasing the health of a plant comprises treating the plant propagules, preferably the seeds of an agricultural, horticultural, ornamental or silivcultural plant selected from the group consisting of transgenic or non-transgenic plants with a mixture according to the present invention.

Consequently, the plant to be treated according to the method of the invention is selected from the group consisting of agricultural, silvicultural and horticultural plants, each in its natural or genetically modified form.

The term "plant (or plants)" is a synonym of the term "crop" which is to be understood as a plant of economic importance and/or a men-grown plant. The term "plant" as used herein includes all parts of a plant such as germinating seeds, emerging seedlings, herbaceous vegetation as well as established woody plants including all belowground portions (such as the roots) and aboveground portions.

In one embodiment, the plant to be treated according to the method of the invention is an agricultural plant. "Agricultural plants" are plants of which a part (e.g. seeds) or all is harvested or cultivated on a commercial scale or which serve as an important source of feed, food, fibres (e.g. cotton, linen), combustibles (e.g. wood, bioethanol, biodiesel, biomass) or other chemical compounds. Preferred agricultural plants are for example cereals, e.g. wheat, rye, barley, triticale, oats, sorghum or rice, beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, oil-seed rape, canola, linseed, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, canola, sugar cane or oil palm; tobacco; nuts; coffee; tea; bananas; vines (table grapes and grape juice grape vines); hop; turf; natural rubber plants.

In a preferred embodiment of the present invention, agricultural plants are field crops such as potatoes, sugar beets, cereals such as wheat, rye, barley, oats, sorghum, rice, corn, cotton, rape, oilseed rape and canola, legumes such as soybeans, peas and field beans, sunflowers, sugar cane, vegetables such as cucumbers, tomatoes, onions, leeks, lettuce and squashes.

In another preferred embodiment of the present invention, the plants to be treated, are selected from soybean, sunflower, corn, cotton, canola, sugar cane, sugar beet, pome fruit, barley, oats, sorghum, rice and wheat.

Consequently, in a preferred embodiment, the plant to be treated according to the method of the invention is selected from soybean, sunflower, corn, cotton, canola, sugar cane, sugar beet, pome fruit, barley, oats, sorghum, rice and wheat.

In an especially preferred embodiment of the present invention, the plants to be treated are selected from wheat, barley, corn, soybean, rice, canola and sunflower. The utmost preferred plant is soybean.

In one embodiment, the plant to be treated according to the method of the invention is a horticultural plant. The term "horticultural plants" are to be understood as plants which are commonly used in horticulture—e.g. the cultivation of ornamentals, vegetables and/or fruits. Examples for ornamentals are turf, geranium, pelargonia, petunia, begonia and fuchsia. Examples for vegetables are potatoes, tomatoes, peppers, cucurbits, cucumbers, melons, watermelons, garlic, onions, carrots, cabbage, beans, peas and lettuce and more preferably from tomatoes, onions, peas and lettuce. Examples for fruits are apples, pears, cherries, strawberry, citrus, peaches, apricots and blueberries.

In one embodiment, the plant to be treated according to the method of the invention is an ornamental plant. "Ornamental plants" are plants which are commonly used in gardening, e.g. in parks, gardens and on balconies. Examples are turf, geranium, pelargonia, petunia, begonia and fuchsia.

In one embodiment, the plant to be treated according to the method of the invention is a silvicultural plants. The term "silvicultural plant" is to be understood as trees, more specifically trees used in reforestation or industrial plantations. Industrial plantations generally serve for the commercial production of forest products, such as wood, pulp, paper, rubber tree, Christmas trees, or young trees for gardening purposes. Examples for silvicultural plants are conifers, like pines, in particular *Pinus* spec., fir and spruce, eucalyptus, tropical trees like teak, rubber tree, oil palm, willow (*Salix*), in particular *Salix* spec., poplar (cottonwood), in particular *Populus* spec., beech, in particular *Fagus* spec., birch, oil palm and oak.

In a preferred embodiment of the invention, the plant to be treated is a herbicide tolerant plant. Within the herbicide tolerant plants, plants tolerant to dicamba are especially preferred.

The term "locus" is to be understood as any type of environment, soil, area or material where the plant is growing or intended to grow as well as the environmental conditions (such as temperature, water availability, radiation) that have an influence on the growth and development of the plant and/or its propagules.

In the terms of the present invention "a mixture" means a combination of two active ingredients. In the present case, a mixture comprises one compound (I) and one compound (II).

The term "genetically modified plants" is to be understood as plants, which genetic material has been modified by the use of recombinant DNA techniques in a way that under natural circumstances it cannot readily be obtained by cross breeding, mutations or natural recombination.

The term "plant propagation material" is to be understood to denote all the generative parts of the plant such as seeds and vegetative plant material such as cuttings and tubers (e.g. potatoes), which can be used for the multiplication of the plant. This includes seeds, grains, roots, fruits, tubers, bulbs, rhizomes, cuttings, spores, offshoots, shoots, sprouts and other parts of plants, including seedlings and young plants, which are to be transplanted after germination or after emergence from soil, meristem tissues, single and multiple plant cells and any other plant tissue from which a complete plant can be obtained.

The term "propagules" or "plant propagules" is to be understood to denote any structure with the capacity to give rise to a new plant, e.g. a seed, a spore, or a part of the vegetative body capable of independent growth if detached from the parent. In a preferred embodiment, the term "propagules" or "plant propagules" denotes for seed.

The term "synergistically" within the term "in synergistically effective amounts" means that the purely additive plant health increasing effects of a simultaneous, that is joint or separate application of one compound (I) and one compound (II), or the successive application of one compound (I) and one compound (II), is surpassed by the application of a mixture according to the invention.

The term "in synergistically effective amounts" means that the amount of the mixture applied according to the invention is suitable to increase the health of a plant in a synergistic manner.

The term "health of a plant" or "plant health" is defined as a condition of the plant and/or its products which is determined by several aspects alone or in combination with each other such as yield, plant vigor, quality and tolerance to abiotic and/or biotic stress.

The below identified indicators for the health condition of a plant may be interdependent or they may result from each other. Each of them is regarded as an individual embodiment of the present invention.

One indicator for the condition of the plant is the yield. "Yield" is to be understood as any plant product of economic value that is produced by the plant such as grains, fruits in the proper sense, vegetables, nuts, grains, seeds, wood (e.g. in the case of silviculture plants) or even flowers (e.g. in the case of gardening plants, ornamentals). The plant products may in addition be further utilized and/or processed after harvesting.

According to the present invention, "increased yield" of a plant, in particular of an agricultural, silvicultural and/or horticultural plant means that the yield of a product of the respective plant is increased by a measurable amount over the yield of the same product of the plant produced under the same conditions, but without the application of the mixture according to the invention.

Increased yield can be characterized, among others, by the following improved properties of the plant:
- increased plant weight
- increased plant height
- increased biomass (higher overall fresh weight (FW))
- increased number of flowers per plant
- higher grain yield
- more tillers
- larger leaves
- increased growth
- increased protein content
- increased oil content
- increased starch content
- increased pigment content According to the present invention, the yield is increased by at least 4%, preferable by 5 to 10%, more preferable by 10 to 20%, or even 20 to 30%. In general, the yield increase may even be higher.

In a preferred embodiment, the mixtures according to the invention are used to synergistically increase the growth of a plant.

In another preferred embodiment, the mixtures according to the invention are used to synergistically increase the biomass of a plant.

Another indicator for the condition of the plant is the plant vigor. The plant vigor becomes manifest in several aspects such as the general visual appearance.

Improved plant vigor can be characterized, among others, by the following improved properties of the plant:
- improved vitality of the plant
- improved plant growth
- improved plant development
- improved visual appearance
- improved plant stand (less plant verse/lodging)
- improved emergence
- enhanced root growth and/or more developed root system
- enhanced nodulation, in particular rhizobial nodulation
- bigger leaf blade
- bigger size
- increased plant weight
- increased plant height
- increased tiller number
- increased number of flowers per plant
- increased shoot growth
- increased yield when grown on poor soils or unfavorable climate
- enhanced photosynthetic activity
- enhanced pigment content (e.g. chlorophyll content)
- earlier flowering
- earlier fruiting
- earlier and improved germination
- earlier grain maturity
- improved self-defence mechanisms
- improved stress tolerance and resistance of the plants against biotic and abiotic stress factors such as fungi, bacteria, viruses, insects, heat stress, cold stress, drought stress, UV stress and/or salt stress
- less non-productive tillers
- less dead basal leaves
- less input needed (such as fertilizers or water)
- greener leaves
- complete maturation under shortened vegetation periods
- less fertilizers needed
- less seeds needed
- easier harvesting
- faster and more uniform ripening
- longer shelf-life
- longer panicles
- delay of senescence
- stronger and/or more productive tillers
- better extractability of ingredients
- improved quality of seeds (for being seeded in the following seasons for seed production)
- reduced production of ethylene and/or the inhibition of its reception by the plant.

The improvement of the plant vigor according to the present invention particularly means that the improvement of any one or several or all of the above mentioned plant characteristics are improved independently of the pesticidal action of the mixture or active ingredients.

In another preferred embodiment, the mixtures according to the invention are used to synergistically improve the plant stand (less plant verse/lodging) of a plant.

In another preferred embodiment, the mixtures according to the invention are used to synergistically enhance the root growth of a plant.

In another preferred embodiment, the mixtures according to the invention are used to synergistically increase the yield of a plant when grown on poor soils or unfavorable climate.

Another indicator for the condition of the plant is the "quality" of a plant and/or its products. According to the present invention, enhanced quality means that certain plant characteristics such as the content or composition of certain ingredients are increased or improved by a measurable or noticeable amount over the same factor of the plant produced under the same conditions, but without the application of the mixtures of the present invention. Enhanced quality can be characterized, among others, by following improved properties of the plant or its product:
- increased nutrient content
- increased protein content
- increased content of fatty acids
- increased metabolite content
- increased carotenoid content
- increased sugar content
- increased amount of essential amino acids
- improved nutrient composition
- improved protein composition
- improved composition of fatty acids
- improved metabolite composition
- improved carotenoid composition
- improved sugar composition
- improved amino acids composition
- improved or optimal fruit color
- improved leaf color
- higher storage capacity higher processability of the harvested products.

In another preferred embodiment, the mixtures according to the invention are used to synergistically increase the sugar content of a plant.

In another preferred embodiment, the mixtures according to the invention are used to synergistically improve the processability of the harvested products of a plant.

Another indicator for the condition of the plant is the plant's tolerance or resistance to biotic and/or abiotic stress factors. Biotic and abiotic stress, especially over longer terms, can have harmful effects on plants. Biotic stress is caused by living organisms while abiotic stress is caused for example by environmental extremes. According to the present invention, "enhanced tolerance or resistance to biotic and/or abiotic stress factors" means (1.) that certain negative factors caused by biotic and/or abiotic stress are diminished in a measurable or noticeable amount as compared to plants exposed to the same conditions, but without being treated with a mixture according to the invention and (2.) that the negative effects are not diminished by a direct action of the mixture according to the invention on the stress factors, e.g. by its fungicidal or insecticidal action which directly destroys the microorganisms or pests, but rather by a stimulation of the plants' own defensive reactions against said stress factors.

Negative factors caused by biotic stress such as pathogens and pests are widely known and range from dotted leaves to total destruction of the plant. Biotic stress can be caused by living organisms, such as:
  pests (for example insects, arachnides, nematodes)
  competing plants (for example weeds)
  microorganisms such as phythopathogenic fungi and/or bacteria
  viruses.

Negative factors caused by abiotic stress are also well-known and can often be observed as reduced plant vigor (see above), for example: dotted leaves, "burned leaves", reduced growth, less flowers, less biomass, less crop yields, reduced nutritional value of the crops, later crop maturity, to give just a few examples. Abiotic stress can be caused for example by:
  extremes in temperature such as heat or cold (heat stress/cold stress)
  strong variations in temperature
  temperatures unusual for the specific season
  drought (drought stress)
  extreme wetness
  high salinity (salt stress)
  radiation (for example by increased UV radiation due to the decreasing ozone layer)
  increased ozone levels (ozone stress)
  organic pollution (for example by phythotoxic amounts of pesticides)
  inorganic pollution (for example by heavy metal contaminants).

As a result of biotic and/or abiotic stress factors, the quantity and the quality of the stressed plants, their crops and fruits decrease. As far as quality is concerned, reproductive development is usually severely affected with consequences on the crops which are important for fruits or seeds. Synthesis, accumulation and storage of proteins are mostly affected by temperature; growth is slowed by almost all types of stress; polysaccharide synthesis, both structural and storage is reduced or modified: these effects result in a decrease in biomass (yield) and in changes in the nutritional value of the product.

In a preferred embodiment, the mixtures according to the invention are used to synergistically increase the biotic stress tolerance of a plant.

In another preferred embodiment, the mixtures according to the invention are used to synergistically increase the tolerance of a plant against bacteria.

In another preferred embodiment, the mixtures according to the invention are used to synergistically increase the tolerance of a plant against virus.

In a preferred embodiment, the mixtures according to the invention are used to synergistically increase the abiotic stress tolerance of a plant.

In yet an even more preferred embodiment, the mixtures according to the invention are used to synergistically increase the drought tolerance of a plant.

In another preferred embodiment, the mixtures according to the invention are used to synergistically increase the tolerance of a plant against ozone stress.

Advantageous properties, obtained especially from treated seeds, are e.g. improved germination and field establishment, better vigor and/or a more homogen field establishment.

As pointed out above, the above identified indicators for the health condition of a plant may be interdependent and may result from each other. For example, an increased resistance to biotic and/or abiotic stress may lead to a better plant vigor, e.g. to better and bigger crops, and thus to an increased yield. Inversely, a more developed root system may result in an increased resistance to biotic and/or abiotic stress. However, these interdependencies and interactions are neither all known nor fully understood and therefore the different indicators are described separately.

In one embodiment the use of the mixtures within the methods according to the invention results in an increased yield of a plant or its product.

In another embodiment the use of the mixtures within the methods according to the invention results in an increased vigor of a plant or its product.

In another embodiment the use of the mixtures within the methods according to the invention results in an increased quality of a plant or its product.

In yet another embodiment the use of the mixtures within the methods according to the invention results in an increased tolerance and/or resistance of a plant or its product against biotic and/or abiotic stress.

In one embodiment of the invention, the tolerance and/or resistance against biotic stress factors is enhanced. Thus, according to a preferred embodiment of the present invention, the inventive mixtures are used for stimulating the natural defensive reactions of a plant against a pathogen and/or a pest. As a consequence, the plant can be protected against unwanted microorganisms such as phytopathogenic fungi and/or bacteria or even viruses and/or against pests such as insects, arachnids and nematodes.

In another embodiment of the invention, the tolerance and/or resistance against abiotic stress factors is enhanced. Thus, according to a preferred embodiment of the present invention, the inventive mixtures are used for stimulating a plant's own defensive reactions against abiotic stress such as extremes in temperature, e.g. heat or cold or strong variations in temperature and/or temperatures unusual for the specific season, drought, extreme wetness, high salinity, radiation (e.g. increased UV radiation due to the decreasing ozone protective layer), increased ozone levels, organic pollution (e.g. by phythotoxic amounts of pesticides) and/or inorganic pollution (e.g. by heavy metal contaminants).

In a preferred embodiment of the invention, the mixtures according to the invention are used for increasing the plant weight, increasing the plants biomass (e.g. overall fresh weight), increasing the grain yield, increasing the number of tillers, for improving the vitality of the plant, improving the plant development, improving the visual appearance, improving the plant stand (less plant verse/lodging), enhancing the root growth and/or improving the development of the root system, increasing the shoot growth, increasing the number of flowers per plant, increasing the yield of the crop when grown on poor soils or unfavorable climates, enhancing photosynthetic activity, enhancing the pigment content, improving the flowering (earlier flowering), improving the germination, improving the stress tolerance and resistance of the plants against biotic and abiotic stress factors such as fungi, bacteria, viruses, insects, heat stress, cold stress, drought stress, UV stress and/or salt stress, decreasing the number of non-productive tillers, decreasing the number of dead basal leaves, improving the greenness of the leaves, reducing the needed input such as fertilizer and water, reducing the seed needed to establish the crop, improving the harvestability of the crop, improving the uniformity of ripening, improving the shelf life, delaying the senescence, strengthening the productive tillers, improving the quality of seeds in seed production, improving fruit color, improving leaf color, improving storage capacity, and/or improving processability of the harvested product.

In another preferred embodiment of the invention, the mixtures according to the invention are used for increasing the plant weight, increasing the plants biomass (e.g. overall fresh weight), increasing the grain yield, increasing the number of tillers, improving the plant development, improving the visual appearance, improving the plant stand (less plant verse/lodging), increasing the yield of the crop when grown on poor soils or unfavorable climates, improving the germination, improving the stress tolerance and resistance of the plants against abiotic stress factors such as cold stress, drought stress, UV stress, decreasing the number of non-productive tillers, decreasing the number of dead basal leaves, improving the greenness of the leaves, reducing the seed needed to establish the crop, improving the harvestability of the crop, improving the shelf life, delaying the senescence, strengthening the productive tillers, and/or improving the quality of seeds in seed production.

It has to be emphasized that the above mentioned effects of the mixtures according to the invention, i.e. enhanced health of the plant, are also present when the plant is not under biotic stress and in particular when the plant is not under pest pressure. It is evident that a plant suffering from fungal or insecticidal attack produces a smaller biomass and leads to a reduced crop yield as compared to a plant which has been subjected to curative or preventive treatment against the pathogenic fungus or any other relevant pest and which can grow without the damage caused by the biotic stress factor. However, the method according to the invention leads to an enhanced plant health even in the absence of any biotic stress. This means that the positive effects of the mixtures of the invention cannot be explained just by the fungicidal and/or herbicidal activities of the compounds (I) and (II), but are based on further activity profiles. Accordingly, in a preferred embodiment of the method, the application of the active ingredients and/or their mixtures is carried out in the absence of pest pressure. But of course, plants under biotic stress can be treated, too, according to the methods of the present invention.

The inventive mixtures are employed by treating the plant, plant propagation material (preferably seed), soil, area, material or environment in which a plant is growing or may grow with an effective amount of the active compounds. The application can be carried out both before and after the infection of the materials, plants or plant propagation materials (preferably seeds) by pests.

In a preferred embodiment of the method, the aerial plant parts are treated with a mixture according to the invention.

Another preferred embodiment of the method comprises seed treatment with compound (II) followed by foliar spraying of the soil, area, material or environment in which a plant is growing or may grow with compound (I).

In one embodiment of the invention, a mixture according to the invention is applied at a growth stage (GS) between GS 00 and GS 65 BBCH of the treated plant.

In a preferred embodiment of the invention, a mixture according to the invention is applied at a growth stage (GS) between GS 00 and GS 55 BBCH of the treated plant.

In an even more preferred embodiment of the invention, a mixture according to the invention is applied at a growth stage (GS) between GS 00 and GS 37 BBCH of the treated plant.

In a most preferred embodiment of the invention, a mixture according to the invention is applied at a growth stage (GS) between GS 00 and GS 21 BBCH of the treated plant.

In one embodiment of the method according to the invention, the plants and/or plant propagules are treated simultaneously (together or separately) or subsequently with a mixture as described above. Of course, the subsequent application is carried out with a time interval which allows a combined action of the applied compounds. Preferably, the time interval for a subsequent application of compound (I) and compound (II) ranges from a few seconds up to 3 months, preferably, from a few seconds up to 1 month, more preferably from a few seconds up to 2 weeks, even more preferably from a few seconds up to 3 days and in particular from 1 second up to 24 hours.

Herein, we have found that simultaneous, that is joint or separate, application of a compound (I) and a compound (II) or the successive application of a compound (I) and a compound (II) allows an enhanced increase of the health of a plant compared to the control rates that are possible with the individual compounds (synergistic mixtures).

In another embodiment of the invention, the mixture as described above is repeatedly applied. If this is the case, the application is repeated two to five times, preferably two times.

When used for increasing the health of a plant, the application rates of the mixtures are between 0.3 g/ha and 3500 g/ha, depending on various parameters such as the treated plant species or the mixture applied. In a preferred embodiment of the method according to the invention, the application rates of the mixtures are between 5 g/ha and 2000 g/ha. In an even more preferred embodiment of the method according to the invention, the application rates of the mixtures are between 20 g/ha and 900 g/ha, in particular from 20 g/ha to 750 g/ha.

In the treatment of plant propagation material (preferably seed), amounts of from 0.01 g to 10 kg, in particular amounts from 0.01 g to 3 kg of mixtures according to the invention are generally required per 100 kilogram of plant propagation material (preferably seed).

As a matter of course, the mixtures according to the invention are used in "effective and non-phytotoxic amounts". This means that they are used in a quantity which allows to obtain the desired effect but which does not give rise to any phytotoxic symptom on the treated plant.

The compounds according to the invention can be present in different crystal modifications whose biological activity may differ. They are likewise subject matter of the present invention.

In all mixtures used according to the methods of the present invention, compounds (I) and compounds (II) are employed in amounts which result in a synergistic effect.

With respect to binary mixtures, the weight ratio of compound (I) to compound (II) is preferably from 200:1 to 1:200, more preferably from 100:1 to 1:100, more preferably from 50:1 to 1:50 and in particular from 20:1 to 1:20. The utmost preferred ratio is 1:10 to 10:1.

The agrochemical mixtures are typically applied as compositions comprising a herbicide as compound (I) and/or a fungicidal compound (II). In a preferred embodiment, the pestical composition comprises a liquid or solid carrier and a mixture as described above.

Plants as well as the propagation material of said plants, which can be treated with the inventive mixtures include all modified non-transgenic plants or transgenic plants, e.g. crops which tolerate the action of herbicides or fungicides or insecticides owing to breeding, including genetic engineering methods, or plants which have modified characteristics in comparison with existing plants, which can be generated for example by traditional breeding methods and/or the generation of mutants, or by recombinant procedures.

For example, mixtures according to the present invention can be applied as seed treatment, foliar spray treatment, in-furrow application or by any other means also to plants which have been modified by breeding, mutagenesis or genetic engineering including but not limiting to agricultural biotech products on the market or in development (cf. http://www-.bio.org/speeches/pubs/er/agri_products.asp).

"Genetically modified plants" are plants, which genetic material has been modified by the use of recombinant DNA techniques in a way that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides. Tolerance to herbicides can be obtained by creating insensitivity at the site of action of the herbicide by expression of a target enzyme which is resistant to herbicide; rapid metabolism (conjugation or degradation) of the herbicide by expression of enzymes which inactivate herbicide; or poor uptake and translocation of the herbicide. Examples are the expression of enzymes which are tolerant to the herbicide in comparison to wild-type enzymes, such as the expression of 5-enolpyruvylshikimate-3-phosphate synthase (EPSPS), which is tolerant to glyphosate (see e.g. Heck et. al, Crop Sci. 45, 2005, 329-339; Funke et. al, PNAS 103, 2006, 13010-13015; U.S. Pat. Nos. 5,188,642, 4,940,835, 5,633,435, 5,804,425, 5,627,061), the expression of glutamine synthase which is tolerant to glufosinate and bialaphos (see e.g. U.S. Pat. Nos. 5,646,024, 5,561,236) and DNA constructs coding for dicamba-degrading enzymes (see for general reference US 2009/0105077, e.g. U.S. Pat. No. 7,105,724 for dicamba resistance in bean, maize (for maize see also WO 08/051633), cotton (for cotton see also U.S. Pat. No. 5,670,454), pea, potatoe, sorghum, soybean (for soybean see also U.S. Pat. No. 5,670,454), sunflower, tobacco, tomato (for tomato see also U.S. Pat. No. 5,670,454)). Furthermore, this comprises also plants tolerant to applications of imidazolinone herbicides (canola (Tan et. al, Pest Manag. Sci 61, 246-257 (2005)); maize (U.S. Pat. Nos. 4,761,373, 5,304,732, 5,331,107, 5,718,079, 6,211, 438, 6,211,439 and 6,222,100, Tan et. al, Pest Manag. Sci 61, 246-257 (2005)); rice (U.S. Pat. Nos. 4,761,373, 5,304,732, 5,331,107, 5,718,079, 6,211,438, 6,211,439 and 6,222,100, S653N (see e.g. US 2003/0217381), S654K (see e.g. US 2003/0217381), A122T (see e.g. WO 04/106529) S653 (At) N, S654 (At)K, A122 (At)T and other resistant rice plants as described in WO 00/27182, WO 05/20673 and WO 01/85970 or U.S. Pat. Nos. 5,545,822, 5,736,629, 5,773,703, 5,773, 704, 5,952,553, 6,274,796); millet (U.S. Pat. Nos. 4,761,373, 5,304,732, 5,331,107, 5,718,079, 6,211,438, 6,211,439 and 6,222,100); barley (U.S. Pat. Nos. 4,761,373, 5,304,732, 5,331,107, 5,718,079, 6,211,438, 6,211,439 and 6,222,100); wheat (U.S. Pat. Nos. 4,761,373, 5,304,732, 5,331,107, 5,718,079, 6,211,438, 6,211,439, 6,222,100, WO 04/106529, WO 04/16073, WO 03/14357, WO 03/13225 and WO 03/14356); sorghum (U.S. Pat. Nos. 4,761,373, 5,304,732, 5,331,107, 5,718,079, 6,211,438, 6,211,439 and 6,222,100); oats (U.S. Pat. Nos. 4,761,373, 5,304,732, 5,331,107, 5,718, 079, 6,211,438, 6,211,439 and 6,222,100); rye (U.S. Pat. Nos. 4,761,373, 5,304,732, 5,331,107, 5,718,079, 6,211,438, 6,211,439 and 6,222,100); sugar beet (WO 98/02526/WO 98/02527); lentils (US 2004/0187178); sunflowers (Tan et. al, Pest Manag. Sci 61, 246-257 (2005))). Gene constructs can be obtained, for example, from microorganism or plants, which are tolerant to said herbicides, such as the *Agrobacterium* strain CP4 EPSPS which is resistant to glyphosate; *Streptomyces* bacteria which are resistance to glufosinate; *Arabidopsis, Daucus carota, Pseudomonoas* spp. or *Zea mais* with chimeric gene sequences coging for HDDP (see e.g. WO 96/38567, WO 04/55191); *Arabidopsis thaliana* which is resistant to protox inhibitors (see e.g. US 2002/0073443).

Examples of commercial available plants with tolerance to herbicides, are the corn varieties "Roundup Ready Corn", "Roundup Ready 2" (Monsanto), "Agrisure GT", "Agrisure GT/CB/LL", "Agrisure GT/RW", "Agrisure 3000GT" (Syngenta), "YieldGard VT Rootworm/RR2" and "YieldGard VT Triple" (Monsanto) with tolerance to glyphosate; the corn varieties "Liberty Link" (Bayer), "Herculex I", "Herculex RW", "Herculex Xtra" (Dow, Pioneer), "Agrisure GT/CB/LL" and "Agrisure CB/LL/RW" (Syngenta) with tolerance to glufosinate; the soybean varieties "Roundup Ready Soybean" (Monsanto) and "Optimum GAT" (DuPont, Pioneer) with tolerance to glyphosate; the cotton varieties "Roundup Ready Cotton" and "Roundup Ready Flex" (Monsanto) with tolerance to glyphosate; the cotton variety "FiberMax Liberty Link" (Bayer) with tolerance to glufosinate; the cotton variety "BXN" (Calgene) with tolerance to bromoxynil; the canola varieties "Navigator" and "Compass" (Rhone-Poulenc) with bromoxynil tolerance; the canola variety "Roundup Ready Canola" (Monsanto) with glyphosate tolerance; the canola variety "InVigor" (Bayer) with glufosinate tolerance; the rice variety "Liberty Link Rice" (Bayer) with glulfosinate tolerance and the alfalfa variety "Roundup Ready Alfalfa" with glyphosate tolerance. Further modified plants with herbicide are commonly known, for instance alfalfa, apple, eucalyptus, flax, grape, lentils, oil seed rape, peas, potato, rice, sugar beet, sunflower, tobacco, tomatom turf grass and wheat with tolerance to glyphosate (see e.g. U.S. Pat. Nos. 5,188,642, 4,940, 835, 5,633,435, 5,804,425, 5,627,061); beans, soybean, cotton, peas, potato, sunflower, tomato, tobacco, corn, sorghum and sugarcane with tolerance to dicamba (see e.g. US 2009/0105077, U.S. Pat. Nos. 7,105,724 and 5,670,454); pepper, apple, tomato, hirse, sunflower, tobacco, potato, corn, cucumber, wheat, soybean and sorghum with tolerance to 2,4-D (see e.g. U.S. Pat. Nos. 6,153,401, 6,100,446, WO 05/107437, U.S. Pat. Nos. 5,608,147 and 5,670,454); sugarbeet, potato, tomato and tobacco with tolerance to gluphosinate (see e.g. U.S. Pat. Nos. 5,646,024, 5,561,236); canola, barley, cotton, juncea, lettuce, lentils, melon, millet, oats, oilseed rape, potato, rice, rye, sorghum, soybean, sugarbeet, sunflower, tobacco, tomato and wheat with tolerance to acetolactate synthase (ALS) inhibiting herbicides, such as triazolopyrimidine sulfonamides, growth inhibitors and imidazolinones (see e.g. U.S. Pat. No. 5,013,659, WO 06/060634, U.S. Pat. Nos. 4,761,373, 5,304,732, 6,211,438, 6,211,439 and 6,222,100); cereal, sugar cane, rice, corn, tobacco, soybean, cotton, rapeseed, sugar beet and potato with tolerance to HPPD inhibitor herbicides (see e.g. WO 04/055191, WO 96/38567, WO 97/049816 and U.S. Pat. No. 6,791,014); wheat, soybean, cotton, sugar beet, oilseed rape, rice, corn, sorghum and sugar cane with tolerance to protoporphyrinogen oxidase (PPO) inhibitor herbicides (see e.g. US 2002/0073443, US 20080052798, Pest Management Science, 61, 2005, 277-285). The methods of producing such herbicide resistant plants are generally known to the person skilled in the art and are described, for example, in the publications mentioned above. Further examples of commercial available modified plants with tolerance to herbicides "CLEARFIELD Corn", "CLEARFIELD Canola", "CLEARFIELD Rice", "CLEARFIELD Lentils", "CLEARFIELD Sunlowers" (BASF) with tolerance to the imidazolinone herbicides.

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood ex-pressly also as pre-toxins, hybrid proteins, truncated or otherwise modified proteins. Hybrid proteins are characterized by a new combination of protein domains, (see e.g. WO 02/015701). Further examples of such toxins or genetically modified plants capable of synthesizing such toxins are disclosed, e.g., in EP A 374 753, WO 93/007278, WO 95/34656, EPA 427 529, EP A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e.g. described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Her-culex® RW (corn cultivars producing Cry34Ab1, Cry35Ab1 and the enzyme Phosphi-nothricin-N-Acetyl-transferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the CryIF toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP A 392 225), plant disease resistance genes (e.g. potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. biomass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

Particularly preferred modified plants suitable to be used in the methods of the present invention are those, which are rendered tolerant to herbicides, in particular tolerant to dicamba.

For use according to the present invention, the inventive mixtures can be converted into the customary formulations, for example solutions, emulsions, suspensions, dusts, powders, pastes and granules. The use form depends on the particular intended purpose; in each case, it should ensure a fine and even distribution of the mixtures accord-ing to the present invention. The formulations are prepared in a known manner (cf. U.S. Pat. No. 3,060,084, EP-A 707 445 (for liquid concentrates), Browning: "Agglomeration", Chemical Engineering, Dec. 4, 1967, 147-48, Perry's Chemical Engineer's Handbook, 4th Ed., McGraw-Hill, New York, 1963, S. 8-57 and ff. WO 91/13546, U.S. Pat. Nos. 4,172,714, 4,144,050, 3,920,442, 5,180,587, 5,232,701, 5,208,030, GB 2,095,558, 3,299,566, Klingman: Weed Control as a Science (J. Wiley & Sons, New York, 1961), Hance et al.: Weed Control Handbook (8th Ed., Blackwell Scientific, Oxford, 1989) and Mollet, H. and Grubemann, A.: Formulation Technology (Wiley VCH Verlag, Weinheim, 2001).

The agrochemical formulations may also comprise auxiliaries which are customary in agrochemical formulations. The auxiliaries used depend on the particular application form and active substance, respectively. Examples for suitable auxiliaries are solvents, solid carriers, dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e.g. for seed treatment formulations). Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e.g. amines such as N-methylpyrrolidone.

Solid carriers are mineral earths such as silicates, silica gels, talc, kaolins, limestone, lime, chalk, bole, loess, clays, dolomite, diatomaceous earth, calcium sulfate, magne-sium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Suitable surfactants (adjuvants, wetters, tackifiers, dispersants or emulsifiers) are alkali metal, alkaline earth metal and ammonium salts of aromatic sulfonic acids, such as lignin-soulfonic acid (Borresperse® types, Borregard, Norway) phenolsulfonic acid, naphthalenesulfonic acid (Morwet® types, Akzo Nobel, U.S.A.), dibutylnaphthalene-sulfonic acid (Nekal® types, BASF, Germany), and fatty acids, alkyl-sulfonates, alkyharylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e.g. methylcellulose), hydrophobically modified starches, polyvinyl alcohols (Mowiol® types, Clariant, Switzerland), polycarboxylates (Sokolan® types, BASF, Germany), polyalkoxylates, polyvi-nylamines (Lupasol® types, BASF, Germany), polyvinylpyrrolidone and the copolymers therof. Examples for thickeners (i. e. compounds that impart a modified flowability to formulations, i.e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA).

Bactericides may be added for preservation and stabilization of the formulation. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie).

Examples for suitable anti-freezing agents are ethylene glycol, propylene glycol, urea and glycerin.

Examples for anti-foaming agents are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof.

Suitable colorants are pigments of low water solubility and water-soluble dyes. Examples to be mentioned and the designations rhodamin B, C. I. pigment red 112, C. I. solvent red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples for tackifiers or binders are polyvinylpyrrolidons, polyvinylacetates, polyvinyl alcohols and cellulose ethers (Tylose®, Shin-Etsu, Japan).

Powders, materials for spreading and dusts can be prepared by mixing or concomitantly grinding the compounds (I) and/or (II) and, if appropriate, further active substances, with at least one solid carrier.

Granules, e.g. coated granules, impregnated granules and homogeneous granules, can be prepared by binding the active substances to solid carriers. Examples of solid carriers are mineral earths such as silica gels, silicates, talc, kaolin, attaclay, limestone, lime, chalk, bole, loess, clay, dolomite, diatomaceous earth, calcium sulfate, magne-sium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Examples for formulation types are:
1. Composition Types for Dilution with Water
i) Water-Soluble Concentrates (SL, LS)

10 parts by weight of compounds of the inventive mixtures are dissolved in 90 parts by weight of water or in a water-soluble solvent. As an alternative, wetting agents or other auxiliaries are added. The active substance dissolves upon dilution with water. In this way, a formulation having a content of 10% by weight of active substance is obtained.
ii) Dispersible Concentrates (DC)

20 parts by weight of compounds of the inventive mixtures are dissolved in 70 parts by weight of cyclohexanone with addition of 10 parts by weight of a dispersant, e.g. polyvinylpyrrolidone. Dilution with water gives a dispersion. The active substance content is 20% by weight.
iii) Emulsifiable Concentrates (EC)

15 parts by weight of compounds of the inventive mixtures are dissolved in 75 parts by weight of xylene with addition of calcium dodecylbenzenesulfonate and castor oil ethoxylate (in each case 5 parts by weight). Dilution with water gives an emulsion. The composition has an active substance content of 15% by weight.

iv) Emulsions (EW, EO, ES)

25 parts by weight of compounds of the inventive mixtures are dissolved in 35 parts by weight of xylene with addition of calcium dodecylbenzenesulfonate and castor oil eth-oxylate (in each case 5 parts by weight). This mixture is introduced into 30 parts by weight of water by means of an emulsifying machine (Ultraturrax) and made into a homogeneous emulsion. Dilution with water gives an emulsion. The composition has an active substance content of 25% by weight.

v) Suspensions (SC, OD, FS)

In an agitated ball mill, 20 parts by weight of compounds of the inventive mixtures are comminuted with addition of 10 parts by weight of dispersants and wetting agents and 70 parts by weight of water or an organic solvent to give a fine active substance sus-pension. Dilution with water gives a stable suspension of the active substance. The active substance content in the composition is 20% by weight.

vi) Water-Dispersible Granules and Water-Soluble Granules (WG, SG)

50 parts by weight of compounds of the inventive mixtures are ground finely with addi-tion of 50 parts by weight of dispersants and wetting agents and prepared as water-dispersible or water-soluble granules by means of technical appliances (e.g. extrusion, spray tower, fluidized bed). Dilution with water gives a stable dispersion or solution of the active substance. The composition has an active substance content of 50% by weight.

vii) Water-Dispersible Powders and Water-Soluble Powders (WP, SP, SS, WS)

75 parts by weight of compounds of the inventive mixtures are ground in a rotor-stator mill with addition of 25 parts by weight of dispersants, wetting agents and silica gel. Dilution with water gives a stable dispersion or solution of the active substance. The active substance content of the composition is 75% by weight.

viii) Gel (GF)

In an agitated ball mill, 20 parts by weight of compounds of the inventive mixtures are comminuted with addition of 10 parts by weight of dispersants, 1 part by weight of a gelling agent wetters and 70 parts by weight of water or of an organic solvent to give a fine suspension of the active substance. Dilution with water gives a stable suspension of the active substance, whereby a composition with 20% (w/w) of active substance is obtained.

2. Composition Types to be Applied Undiluted ix) Dustable Powders (DP, DS)

5 parts by weight of compounds of the inventive mixtures are ground finely and mixed intimately with 95 parts by weight of finely divided kaolin. This gives a dustable composition having an active substance content of 5% by weight.

x) Granules (GR, FG, GG, MG)

0.5 parts by weight of compounds of the inventive mixtures is ground finely and associ-ated with 99.5 parts by weight of carriers. Current methods are extrusion, spray-drying or the fluidized bed. This gives granules to be applied undiluted having an active sub-stance content of 0.5% by weight.

xi) ULV Solutions (UL)

10 parts by weight of compounds of the inventive mixtures are dissolved in 90 parts by weight of an organic solvent, e.g. xylene. This gives a composition to be applied undiluted having an active substance content of 10% by weight.

The agrochemical formulations generally comprise between 0.01 and 95%, preferably between 0.1 and 90%, most preferably between 0.5 and 90%, by weight of active substances. The compounds of the inventive mixtures are employed in a purity of from 90% to 100%, preferably from 95% to 100% (according to NMR spectrum).

The compounds of the inventive mixtures can be used as such or in the form of their compositions, e.g. in the form of directly sprayable solutions, powders, suspensions, dispersions, emulsions, oil dispersions, pastes, dustable products, materials for spreading, or granules, by means of spraying, atomizing, dusting, spreading, brushing, immersing or pouring. The application forms depend entirely on the intended purposes; it is intended to ensure in each case the finest possible distribution of the compounds present in the inventive mixtures.

Aqueous application forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active substance concentrations in the ready-to-use preparations can be varied within relatively wide ranges. In general, they are from 0.0001 to 10%, preferably from 0.001 to 1% by weight of compounds of the inventive mixtures.

The compounds of the inventive mixtures may also be used successfully in the ultra-low-volume process (ULV), it being possible to apply compositions comprising over 95% by weight of active substance, or even to apply the active substance without additives.

Various types of oils, wetters, adjuvants, herbicides, fungicides, other pesticides, or bactericides may be added to the active compounds, if appropriate not until immediately prior to use (tank mix). These agents can be admixed with the compounds of the inventive mixtures in a weight ratio of 1:100 to 100:1, preferably 1:10 to 10:1.

Compositions of this invention may also contain fertilizers such as ammonium nitrate, urea, potash, and superphosphate, phytotoxicants and plant growth regulators and safeners. These may be used sequentially or in combination with the above-described compositions, if appropriate also added only immediately prior to use (tank mix). For example, the plant(s) may be sprayed with a composition of this invention either before or after being treated with the fertilizers.

The compounds contained in the mixtures as defined above can be applied simultaneously, that is jointly or separately, or in succession, the sequence, in the case of separate application, generally not having any effect on the result of the control measures.

According to this invention, applying one compound (I) and one compound (II) is to be understood to denote, that one compound (I) and one compound (II) occur simultaneously at the site of action (i.e. plant, plant propagation material (preferably seed), soil, area, material or environment in which a plant is growing or may grow) in a effective amount.

This can be obtained by applying one compound (I) and one compound (II) simultaneously, either jointly (e.g. as tank-mix) or separately, or in succession, wherein the time interval between the individual applications is selected to ensure that the active substance ap-plied first still occurs at the site of action in a sufficient amount at the time of application of the further active substance(s). The order of application is not essential for working of the present invention.

In the inventive mixtures, the weight ratio of the compounds generally depends from the properties of the compounds of the inventive mixtures.

The compounds of the inventive mixtures can be used individually or already partially or completely mixed with one another to prepare the composition according to the invention. It is also possible for them to be packaged and used further as combination composition such as a kit of parts.

In one embodiment of the invention, the kits may include one or more, including all, components that may be used to prepare a subject agrochemical composition. E.g., kits may include the compound (I) and compound (II) and/or an adjuvant component and/or a further pesticidal compound (e.g. insecticide, fungicide or herbicide) and/or a growth regulator component). One or more of the components may already be combined together or preformulated. In those embodiments where more than two components are provided in a kit, the components may already be combined together and as such are packaged in a single container such as a vial, bottle, can, pouch, bag or canister. In other embodiments, two or more components of a kit may be packaged sepa-rately, i.e., not preformulated. As such, kits may include one or more separate containers such as vials, cans, bottles, pouches, bags or canisters, each container containing a separate component for an agrochemical composition. In both forms, a component of the kit may be applied separately from or together with the further components or as a component of a combination composition according to the invention for preparing the composition according to the invention.

The user applies the composition according to the invention usually from a predosage device, a knapsack sprayer, a spray tank or a spray plane. Here, the agrochemical composition is made up with water and/or buffer to the desired application concentration, it being possible, if appropriate, to add further auxiliaries, and the ready-to-use spray liquid or the agrochemical composition according to the invention is thus obtained. Usually, 50 to 500 liters of the ready-to-use spray liquor are applied per hectare of agricultural useful area, preferably 50 to 400 liters.

According to one embodiment, individual compounds of the inventive mixtures formulated as composition (or formulation) such as parts of a kit or parts of the inventive mixture may be mixed by the user himself in a spray tank and further auxiliaries may be added, if appropriate (tank mix).

In a further embodiment, either individual compounds of the inventive mixtures formulated as composition or partially premixed components, e.g. components comprising the compound (I) and compound (II) may be mixed by the user in a spray tank and further auxiliaries and additives may be added, if appropriate (tank mix).

In a further embodiment, either individual components of the composition according to the invention or partially premixed components, e.g. components comprising the compound (I) and compound (II), can be applied jointly (e.g. after tankmix) or consecutively.

The term "synergistically effective amount" denotes an amount of the inventive mixtures, which is sufficient for achieving the synergistic plant health effects, in particular the yield effects as defined herein. More exemplary information about amounts, ways of application and suitable ratios to be used is given below. Anyway, the skilled artisan is well aware of the fact that such an amount can vary in a broad range and is dependent on various factors, e.g. the treated cultivated plant or material and the climatic conditions.

When preparing the mixtures, it is preferred to employ the pure active compounds, to which further active compounds against pests, such as insecticides, herbicides, fungicides or else herbicidal or growth-regulating active compounds or fertilizers can be added as further active components according to need.

Seed treatment can be made into the seedbox before planting into the field.

For seed treatment purposes, the weight ration in the binary and ternary mixtures of the present invention generally depends from the properties of the compounds of the inventive mixtures.

Compositions, which are especially useful for seed treatment are e.g.:
A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-formulations (GF)
I Dustable powders (DP, DS)

These compositions can be applied to plant propagation materials, particularly seeds, diluted or undiluted. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying or treating agrochemical compounds and com-positions thereof, respectively, on to plant propagation material, especially seeds, are known in the art, and include dressing, coating, pelleting, dusting and soaking applica-tion methods of the propagation material (and also in furrow treatment). In a preferred embodiment, the compounds or the compositions thereof, respectively, are applied on to the plant propagation material by a method such that germination is not induced, e.g. by seed dressing, pelleting, coating and dusting.

In the treatment of plant propagation material (preferably seed), the application rates of the inventive mixture are generally for the formulated product (which usually comprises from 10 to 750 g/l of the active(s)).

The invention also relates to the propagation products of plants, and especially the seed comprising, that is, coated with and/or containing, a mixture as defined above or a composition containing the mixture of two or more active ingredients or a mixture of two or more compositions each providing one of the active ingredients. The plant propagation material (preferably seed) comprises the inventive mixtures in an amount of from 0.01 g to 10 kg per 100 kg of plant propagation material (preferably seed).

The separate or joint application of the compounds of the inventive mixtures is carried out by spraying or dusting the seeds, the seedlings, the plants or the soils before or after sowing of the plants or before or after emergence of the plants.

The following examples are intended to illustrate the invention, but without imposing any limitation.

EXAMPLES

Example 1

The effect of fluxapyroxad solo, dicamba solo and a mixture comprising both compounds on the growth (biomass) of cucumber cotyledons was evaluated.

Cucumbers were sown and germinated in the dark at 21.5° C. and 97% relative humidity for 4 days. Subsequently, 20 to 30 cotyledons per treatment were cut and placed in a Petri dish containing 10 ml of the treatment solution as described below. The active ingredients were dissolved in 0.5% DMSO and diluted to the concentrations given in table 2. Control cotyledons were treated with the 0.5% DMSO solution only. Following the incubation in the dark at 21.5° C. for 4 days the cotyledons were weight and the fresh biomass recorded (table 2). Only those cotyledons were used for the measurement which did not show any macerating reaction.

The efficacy of the tested active ingredients was calculated as % of biomass increase compared to the control:

$$E=(a/b-1)\cdot 100$$

a corresponds to biomass of cotyledons after incubation in the treated plants in g; and
b corresponds to biomass of cotyledons after incubation in the control in g.

An efficacy of 0 means the biomass in the treated cotyledons corresponds to that of the untreated control; an efficacy of 100 means the treated plants showed an increase in biomass of 100%.

The expected efficacies of the combinations of the active ingredients were estimated using Colby's formula (Colby, S. R., Calculating synergistic and antagonistic responses of herbicide combinations, Weeds, 15, pp. 20-22, 1967) and compared with the observed efficacies.

$$E=x+y-x\cdot y/100 \quad \text{Colby's formula}$$

E expected efficacy, expressed in % of the untreated control, when using the mixture of the active compounds A and B at the concentrations a and b
x efficacy, expressed in % of the untreated control, when using the active ingredient A at the concentration a
y efficacy, expressed in % of the untreated control, when using the active ingredient B at the concentration b

TABLE 2

Biomass of cotyledons treated or not treated with fluxapyroxad, dicamba or a mixture comprising both compounds

| Treatments | Mean cotyledon biomass [mg] | Observed efficacy (%) | Expected efficacy (%) | Synergism (%) |
|---|---|---|---|---|
| 0.5% DMSO | 48.0 | | | |
| Fluxapyroxad (5 ppm) | 47.1 | −1.9 | | |
| Dicamba (1.25 ppm) | 48.2 | 0.2 | | |
| Fluxapyroxad (5 ppm) + dicamba (1.25 ppm) | 49.1 | 2.2 | −1.7* | 3.8 |

*according to Colby's formula

There was no stimulation of the growth of the cotyledons by either fluxapyroxad or dicamba when applied alone, but an increase in cotyledon growth was surprisingly observed when fluxapyroxad and dicamba were applied as a mixture according to the present invention. The observed efficacy in growth stimulation is higher compared to the expected efficacy, as can be seen in table 2. Clearly, the mixture of fluxapyroxad and dicamba has a synergistic effect on the stimulation of growth (biomass) as could be shown in the experiment presented above.

Example 2

The transpiration as an direct indicator of water stress of wheat plants treated or not treated with fluxapyroxad solo, dicamba solo, and respective mixtures thereof was assessed. 10 to 14 days old wheat plants were cut above the ground and placed into Eppendorf caps containing 2.2 ml of the test solution as described below. The wheat plants were incubated for 24 h at 25° C. and 50% relative humidity in a growth chamber. The weight of the Eppendorf cap including the test solution but excluding the plant was assessed before and after incubation. The difference in weight was recorded as the loss of water through transpiration. This assay was used to access the drought tolerance of the plants.

In the present example wheat plants of the variety 'Monopol' were grown at 18° C. for 10 days in the greenhouse prior to the treatment and the incubation. 10 plants per treatment were treated and incubated as described. Fluxapyroxad and dicamba were dissolved on 0.5% DMSO. The tested concentrations are described in table 3. Control plants were treated with the blank 0.5% DMSO solution only.

The efficacy of the tested compounds and mixtures was calculated as % of water loss compared to the control:

$$E=(a/b-1)\cdot 100$$

a corresponds to water loss of plants after incubation in the treated plants in g and
b corresponds to water loss of plants after incubation in the control in g.

An efficacy of 0 means the water loss, i.e. transpired water, in the treated plants corresponds to that of the untreated control; an efficacy of 100 means the treated plants showed a decrease of transpired water of 100%.

The expected efficacies of the combinations of the compounds were estimated using Colby's formula (Colby, S. R., Calculating synergistic and antagonistic responses of herbicide combinations, Weeds, 15, pp. 20-22, 1967) and compared with the observed efficacies.

$$E=x+y-x\cdot y/100 \quad \text{Colby's formula}$$

E expected efficacy, expressed in % of the untreated control, when using the mixture of the active compounds A and B at the concentrations a and b
x efficacy, expressed in % of the untreated control, when using the active ingredient A at the concentration a
y efficacy, expressed in % of the untreated control, when using the active ingredient B at the concentration b

TABLE 3

Water loss through transpiration of plants treated or not treated with fluxapyroxad, dicamba or a mixture comprising both compounds.

| Treatments | Mean water loss [g] | Observed efficacy (%) | Expected efficacy (%) | Synergism (%) |
|---|---|---|---|---|
| 0.5% DMSO | 0.745 | 0.00 | | |
| Fluxapyroxad (10 ppm) | 1.061 | −42.4 | | |
| Fluxapyroxad (50 ppm) | 0.660 | 11.5 | | |
| Fluxapyroxad (100 ppm) | 0.607 | 18.5 | | |
| Dicamba (1.25 ppm) | 0.781 | −4.8 | | |
| Dicamba (12.5 ppm) | 0.765 | −2.7 | | |
| Dicamba (125 ppm) | 0.737 | 1.1 | | |
| Fluxapyroxad (10 ppm) + dicamba (1.25 ppm) | 0.673 | 9.7 | −49.3 | 59.0 |
| Fluxapyroxad (10 ppm) + dicamba (125 ppm) | 0.701 | 5.9 | −40.8 | 46.7 |
| Fluxapyroxad (50 ppm) + dicamba (12.5 ppm) | 0.609 | 18.3 | 9.1 | 9.2 |
| Fluxapyroxad (50 ppm) + dicamba (125 ppm) | 0.629 | 15.6 | 12.5 | 3.1 |
| Fluxapyroxad (100 ppm) + dicamba (1.25 ppm) | 0.498 | 33.2 | 14.6 | 18.6 |
| Fluxapyroxad (100 ppm) + dicamba (12.5 ppm) | 0.497 | 33.3 | 16.3 | 17.0 |

TABLE 3-continued

Water loss through transpiration of plants treated or not treated with fluxapyroxad, dicamba or a mixture comprising both compounds.

| Treatments | Mean water loss [g] | Observed efficacy (%) | Expected efficacy (%) | Synergism (%) |
|---|---|---|---|---|
| Fluxapyroxad (100 ppm) + dicamba (125 ppm) | 0.555 | 25.5 | 19.4 | 6.1 |

*according to Colby's formula

Lower concentrations of fluxapyroxad or dicamba when applied alone resulted in an increased transpiration (water loss). Higher concentrations of fluxapyroxad when applied alone, however, decreased transpiration. A significant decrease in transpiration was surprisingly observed when fluxapyroxad and dicamba were applied as a mixture according to the invention. The observed efficacy in reduction of transpiration was higher compared to the expected efficacy, as can be seen in table 3. Noticeably, the mixture according to the invention, comprising fluxapyroxad and dicamba results in a synergistic increase of drought tolerance (expressed as the reduction in transpiration or water loss) as could be clearly shown in the experiment presented.

Example 3

The relative weight loss of wheat leaves treated or not treated with fluxapyroxad, dicamba, and mixtures thereof as an indirect parameter for increased drought tolerance was assessed. Leaves of 10 to 14 days old wheat plants were detached and placed into Eppendorf caps containing 2.2 ml of the test solution as described below. The wheat leaves were incubated for 24 h at 25° C. and 50% relative humidity in a growth chamber. After incubation, the incubated leaves were removed from the solution and placed on filter paper in a growth chamber for 60 minutes (25° C., 50% rel. humidity). Fresh biomass of the leaves was assessed directly after incubation and in addition after 60 minutes. The difference in fresh weight was recorded as relative weight loss. The relative loss of fresh weight is calculated as:

$$\text{fresh weight loss } [\%] = \left(1 - \frac{FW_{end}}{FW_{begin}}\right) \times 100\%$$

In the present example wheat plants of the variety 'Monopol' were grown at 18° C. for 10 days in the greenhouse prior to the treatment and the incubation. 10 plants per treatment were treated and incubated as described. Fluxapyroxad and dicamba were dissolved on 0.5% DMSO. Tested concentrations are described in table 4. Control plants were treated with the blank 0.5% DMSO solution only.

The efficacy of the tested compounds and mixtures was calculated as % of relative weight loss compared to the control:

$$E=(1-a/b)\cdot 100$$

a corresponds to relative weight loss of leaves after incubation in the treated plants in g; and
b corresponds to relative weight loss of leaves after incubation in the control in g.

An efficacy of 0 means the relative weight loss in the treated leaves corresponds to that of the untreated control; an efficacy of 100 means the treated leaves showed a decrease of relative weight loss of 100%.

The expected efficacies of the combinations of the compounds were estimated using Colby's formula (Colby, S. R., Calculating synergistic and antagonistic responses of herbicide combinations, Weeds, 15, pp. 20-22, 1967) and compared with the observed efficacies.

$$E=x+y-x\cdot y/100 \qquad \text{Colby's formula}$$

E expected efficacy, expressed in % of the untreated control, when using the mixture of the active compounds A and B at the concentrations a and b
x efficacy, expressed in % of the untreated control, when using the active ingredient A at the concentration a
y efficacy, expressed in % of the untreated control, when using the active ingredient B at the concentration b

TABLE 4

Relative loss of fresh biomass of wheat leaves treated or not treated with fluxapyroxad solo, dicamba solo or a mixture comprising both compounds

| Treatments | Mean relative weight loss [%] | Observed efficacy (%) | Expected efficacy (%) | Synergism (%) |
|---|---|---|---|---|
| 0.5% DMSO | 19.14% | 0.00 | | |
| Fluxapyroxad (10 ppm) | 17.62% | 7.94 | | |
| Fluxapyroxad (50 ppm) | 13.61% | 28.89 | | |
| Dicamba (1.25 ppm) | 17.09% | 10.69 | | |
| Dicamba (12.5 ppm) | 15.74% | 17.76 | | |
| Fluxapyroxad (10 ppm) + dicamba (1.25 ppm) | 13.52% | 29.35 | 17.78 | 11.57 |
| Fluxapyroxad (10 ppm) + dicamba (125 ppm) | 12.25% | 35.97 | 21.87 | 14.10 |
| Fluxapyroxad (50 ppm) + dicamba (12.5 ppm) | 11.14% | 41.77 | 41.52 | 0.25 |

*according to Colby's formula

Fluxapyroxad and dicamba reduced fresh weight loss when applied alone. However, a much stronger decrease in loss of fresh biomass was observed when fluxapyroxad and dicamba were applied as a mixture according to the present invention. The observed efficacy in reduction of relative weight loss is higher compared to the expected efficacy, as can be seen in table 4. Clearly, the mixture of fluxapyroxad and dicamba has a synergistic effect on drought tolerance expressed as the reduction in relative weight loss of fresh biomass.

The invention claimed is:

1. A method for improving the health of a plant comprising improving plant yield, vigor, quality and tolerance to abiotic and/or biotic stress, wherein the plant, the locus where the plant is growing or is expected to grow or plant propagation material from which the plant grows is treated with a synergistically effective amount of
   1) a herbicidal compound (I) selected from the group consisting of chloramben, dicamba, 2,3,6-TBA, quinclorac and quinmerac; and
   2) a fungicidal compound (II) selected from the group consisting of N-(3',4',5'-trifluorobiphenyl-2-yl)-3-difluoromethyl-1-methyl-1H-pyrazole-4-carboxamide (common name: fluxapyroxad), N-[2-(4'-trifluoromethylthio)-biphenyl]-3-difluoromethyl-1-methyl-1H-pyrazole-4-carboxamide, N-(3',4'-dichloro-5-fluorobiphenyl-2-yl)-3-difluoromethyl-1-methylpyrazole-4-carboxamide (common name: bixafen), N-[2-(1,3-dimethylbutyl)-phenyl]-1,3-dimethyl-5-fluoro-1H-pyrazole-4-carboxamide (common name: penflufen), N-(2-bicyclopropyl-2-yl-phenyl)-3-di fluoromethyl-1-methyl-1H-pyrazole-4-carboxamide (common name:

sedaxane), N-[1,2,3,4-tetrahydro-9-(1-methylethyl)-1,4-methanonaphthalen-5-yl]-3-(difluoromethyl)-1-methyl-1H-pyrazole-4-carboxamide (common name: isopyrazam), furametpyr, and thifluzamide;

wherein said compounds are applied simultaneously, that is jointly or separately, or successively; and wherein the plant is selected from soybean, sunflower, corn, cotton, canola, sugar cane, sugar beet, pome fruit, barley, oats, sorghum, rice and wheat.

2. The method according to claim 1, wherein compound (I) is dicamba.

3. The method according to claim 1, wherein the fungicidal compound (II) is selected from the group consisting of fluxapyroxad, bixafen, and isopyrazam.

4. The method according to claim 1, wherein the fungicidal compound (II) is fluxapyroxad.

5. The method according to claim 1, wherein the pesticidal composition further comprises a liquid or solid carrier.

6. The method according to claim 1, wherein the compounds are repeatedly applied.

7. The method according to claim 1, wherein the plant is selected from the group consisting of agricultural, silvicultural and horticultural plants, each in its natural or genetically modified form.

8. The method according to claim 1, wherein the plant is a herbicide tolerant plant.

9. A method according to claim 8, wherein the plant is a dicamba tolerant plant.

* * * * *